(12) United States Patent
Carn

(10) Patent No.: US 6,652,771 B2
(45) Date of Patent: Nov. 25, 2003

(54) PHASE CHANGE MATERIAL BLEND, METHOD FOR MAKING, AND DEVICES USING SAME

(76) Inventor: Ronald M. Carn, 3448 Grey Cape Ct., Redding, CA (US) 96003

(*) Notice: Subject to any disclaimer, the term of this patent is extended or adjusted under 35 U.S.C. 154(b) by 72 days.

(21) Appl. No.: 10/074,749

(22) Filed: Feb. 12, 2002

(65) Prior Publication Data

US 2003/0012947 A1 Jan. 16, 2003

Related U.S. Application Data

(60) Provisional application No. 60/304,733, filed on Jul. 11, 2001.

(51) Int. Cl.$^7$ ................................................. C09K 5/14
(52) U.S. Cl. ............................... 252/70; 62/4; 62/530; 165/104.12; 165/104.15; 165/104.17; 165/920; 607/96; 607/114
(58) Field of Search .................. 252/70; 62/4, 530; 165/104.12, 104.15, 104.17, 920; 607/96, 114

(56) References Cited

U.S. PATENT DOCUMENTS

| | | | |
|---|---|---|---|
| 3,823,089 A | | 7/1974 | Ryan et al. |
| 3,977,202 A | | 8/1976 | Forusz et al. |
| 3,980,070 A | | 9/1976 | Krupa |
| 4,003,426 A | | 1/1977 | Best et al. |
| 4,008,170 A | | 2/1977 | Allan |
| 4,182,398 A | | 1/1980 | Salyer et al. |
| 4,205,685 A | | 6/1980 | Yoshida et al. |
| 4,237,023 A | | 12/1980 | Johnson et al. |
| 4,247,240 A | | 1/1981 | Schora, Jr. et al. |
| 4,253,983 A | | 3/1981 | Blanie |
| 4,259,198 A | | 3/1981 | Kreibich et al. |
| 4,259,401 A | | 3/1981 | Chahroudi et al. |
| 4,273,667 A | | 6/1981 | Kent et al. |
| 4,292,189 A | | 9/1981 | Chen |
| 4,294,078 A | | 10/1981 | MacCracken |
| 4,367,788 A | | 1/1983 | Cordon |
| 4,463,799 A | | 8/1984 | Takahashi et al. |
| 4,470,917 A | | 9/1984 | Hawe et al. |
| 4,504,402 A | | 3/1985 | Chen et al. |
| 4,505,953 A | | 3/1985 | Chen et al. |
| 4,513,053 A | | 4/1985 | Chen et al. |
| 4,545,916 A | | 10/1985 | Chalk et al. |
| 4,561,989 A | | 12/1985 | Wada et al. |
| 4,567,877 A | | 2/1986 | Sepahpur |
| 4,587,279 A | | 5/1986 | Salyer et al. |
| 4,603,106 A | | 7/1986 | Cerami et al. |
| 4,617,332 A | | 10/1986 | Salyer et al. |
| 4,668,564 A | | 5/1987 | Orchard |
| 4,671,267 A | | 6/1987 | Stout |
| 4,680,173 A | | 7/1987 | Burger |
| 4,708,812 A | | 11/1987 | Hatfield |
| 4,711,813 A | | 12/1987 | Salyer |
| 4,747,240 A | | 5/1988 | Voisinet et al. |
| 4,851,291 A | | 7/1989 | Vigo et al. |
| 4,964,402 A | | 10/1990 | Grim et al. |
| 5,106,520 A | | 4/1992 | Salyer |
| 5,211,949 A | | 5/1993 | Salyer |
| 5,531,777 A | * | 7/1996 | Goldstein et al. |
| 5,545,197 A | * | 8/1996 | Bowen |
| 5,641,325 A | * | 6/1997 | Delk et al. |
| 5,792,213 A | * | 8/1998 | Bowen |
| 5,843,145 A | * | 12/1998 | Brink |

FOREIGN PATENT DOCUMENTS

| | | |
|---|---|---|
| DE | 2643895 | 3/1978 |
| DE | 3045842 | 7/1982 |
| EP | 0022717 | 4/1982 |
| FR | 2368529 | 5/1978 |
| JP | 54042380 | 4/1979 |
| JP | 59142276 | 8/1984 |
| JP | 59170180 | 9/1984 |
| JP | 59232164 | 12/1984 |
| JP | 60086188 | 5/1985 |
| JP | 60086191 | 5/1985 |

OTHER PUBLICATIONS

Theng, *The Chemistry of Clay–Organic Reactions*, John Wiley & Sons, New York, pp. 13–15 and 18–20 (1974) (no month).

* cited by examiner

*Primary Examiner*—Anthony J. Green
(74) *Attorney, Agent, or Firm*—Nixon Peabody LLP

(57) ABSTRACT

The present invention relates to a powdered mix of a phase change material blend. The blend includes a polar phase change material bound substantially to at least one surface of a clay matrix having a surface charge, wherein the blend is present in a powdered form at temperatures above and below the phase change temperature of the polar phase change material. The present invention also relates to a method of making the powdered mix of a phase change material blend and a therapy pack including the powdered mix of a phase change material blend.

21 Claims, 2 Drawing Sheets

PHASE CHANGE MATERIAL BLEND, METHOD FOR MAKING, AND DEVICES USING SAME

The present invention claims the benefit of U.S. Provisional patent application Ser. No. 60/304,733, filed Jul. 11, 2001, which is hereby incorporated by reference in its entirety.

FIELD OF THE INVENTION

The present invention relates to blends of phase change materials and clay matrices, methods of making them, and devices using the blends.

BACKGROUND OF THE INVENTION

Phase change materials (PCMs) are well known materials that utilize their latent heat of fusion to absorb, store, and release thermal energy during phase conversions between solid and liquid phases. In particular, a PCM absorbs/releases a large quantity of energy in the vicinity of its melting/freezing point, i.e. phase change temperature, however, the temperature of the substance itself remains about the same. These latent heats of fusion are greater than the sensible heat capacities of the materials. More specifically, upon melting and freezing, per unit weight, a PCM absorbs and releases substantially more energy than a sensible heat storage material that is heated or cooled to the same temperature range. The latent heat of fusion of many PCMs is substantial and can be used as a heat source or a heat sink. Thus, various PCMs have been applied in building structures, solar collectors, thermal energy storage (TES) units, road base materials, beverage and food containers, orthopedic devices, medical wraps, and textile applications such as garments.

For example, U.S. Pat. No. 4,711,813 to Salyer, discloses a polyethylene composite formed from cross-linked polyethylene having a straight chain (crystalline) alkyl hydrocarbon incorporated therein as a phase change material which may be manufactured as pellets or in sheet form. The polyethylene composite is useful for incorporation into concrete or other building materials and is used for wall or floor coverings, fire retardants, or runway, roadway or bridge de-icing, and the like.

U.S. Pat. No. 4,617,332 to Salyer describes a phase change composition comprising a matrix material selected from the group consisting of hydraulic cement, gypsum, lime, and plaster of paris, and a plurality of pellets or granules containing a crystalline straight chain alkyl hydrocarbon or a mixture of crystalline, straight chain, alkyl hydrocarbons with the hydrocarbons having at least 14 carbon atoms and a heat of fusion greater than 30 cal/g.

U.S. Pat. No. 4,504,402 to Chen et al. discloses encapsulated phase change materials in pellets for incorporation into concrete or other building materials. The encapsulated phase change compositions may be a Glauber salt eutectic mixture, sodium hydroxide, polyethylene, sodium sulfate decahydrate, sodium thiosulfate pentahydrate, calcium chloride hexahydrate, magnesium nitrate hexahydrate, the eutectic of magnesium nitrate hexahydrate and ammonium nitrate, potassium fluoride tetrahydrate, sodium acetate trihydrate, stearic acid, the eutectic of naphthalene and benzoic acid, and paraffinic hydrocarbons. Shell materials described in the patent include a copolymer latex of butadieneacrylonitrile, a copolymer of vinylidene chloride-acrylic, resinous latexes, rubber latexes, epoxy polymers, polyurethane polymers, acrylic polymers, cellulose acetate, and polyamides.

U.S. Pat. No. 4,708,812 to Hatfield discloses encapsulated phase change material particles, such as a crystalline polymer, naphthalene, salt hydrate, and a crystalline paraffin.

U.S. Pat. No. 4,587,279 to Salyer describes a composition comprising an inorganic building material and an end-capped polyethylene glycol dispersed therein as a phase change material.

One of the basic problems, however, with the use of solid-to-liquid PCMs for temperature control, is containment. In particular, for solid-to-liquid PCMs, the PCM exists as a solid phase PCM below the PCM melting point, in the form of a thick block or agglomeration, and as a liquid phase PCM above the PCM melting point. Particular problems are associated with the presence of a liquid phase PCM, such as leakage.

U.S. Pat. Nos. 5,211,949 and 5,106,520, both to Salyer, disclose a conformable, powder-like mix of silica particles having a critical size of about 0.007 to about 0.07 microns, as a matrix, and a PCM. The mix does not tend to solidify at temperatures below the PCM melting point and does not liquefy at temperatures above the PCM melting point. However, the spherical silica particles are relatively expensive, difficult to process, and are very hygroscopic, necessitating special packaging materials.

Accordingly, there is still a need for a phase change material blend using an economical and readily available matrix and that can be provided in a loosely bound or powder-like form. The present invention is directed to overcoming these and other deficiencies in the art.

SUMMARY OF THE INVENTION

The present invention relates to a powdered mix of a phase change material blend. The blend includes a polar phase change material bound substantially to at least one surface of a clay matrix having a surface charge, wherein the blend is present in a powdered form at temperatures above and below the phase change temperature of the polar phase change material.

The present invention also relates to a method of making a powdered mix of a phase change material blend. The method includes mixing a clay matrix having a surface charge with a polar phase change material under conditions effective to bind the polar phase change material substantially to at least one surface of the clay matrix in a powdered form at temperatures above and below the phase change temperature of the polar phase change material.

Another embodiment of the present invention relates to a therapy pack including an outer material encapsulating a powdered mix of a phase change material blend, wherein the phase change material blend includes a polar phase change material bound substantially to at least one surface of a clay matrix having a surface charge and wherein the blend is present in a powdered form at temperatures above and below the phase change temperature of the polar phase change material.

The phase change material blend of the present invention utilizes a clay matrix as a substrate for a polar phase change material (PCM) that remains loosely bound or powder-like, at temperatures above and below the phase change temperature of the PCM. In particular, the clay matrix-PCM blend will not liquefy upon heating of the PCM above its melting point and will not form a rigid solid at temperatures below the melting point of the PCM (i.e., the blend is powder-like throughout the temperature range). The PCM can change phase while bound to the clay matrix and can utilize its latent heat of fusion to absorb, store, and release heat or cool during such phase conversions. The blend of the present invention uses an economical, readily available, and naturally occurring matrix for the PCM. In addition, the consistency of the blend can be varied according to the type of clay matrix used and the size of the particles in the clay matrix.

DETAILED DESCRIPTION OF THE INVENTION

Figure 1:
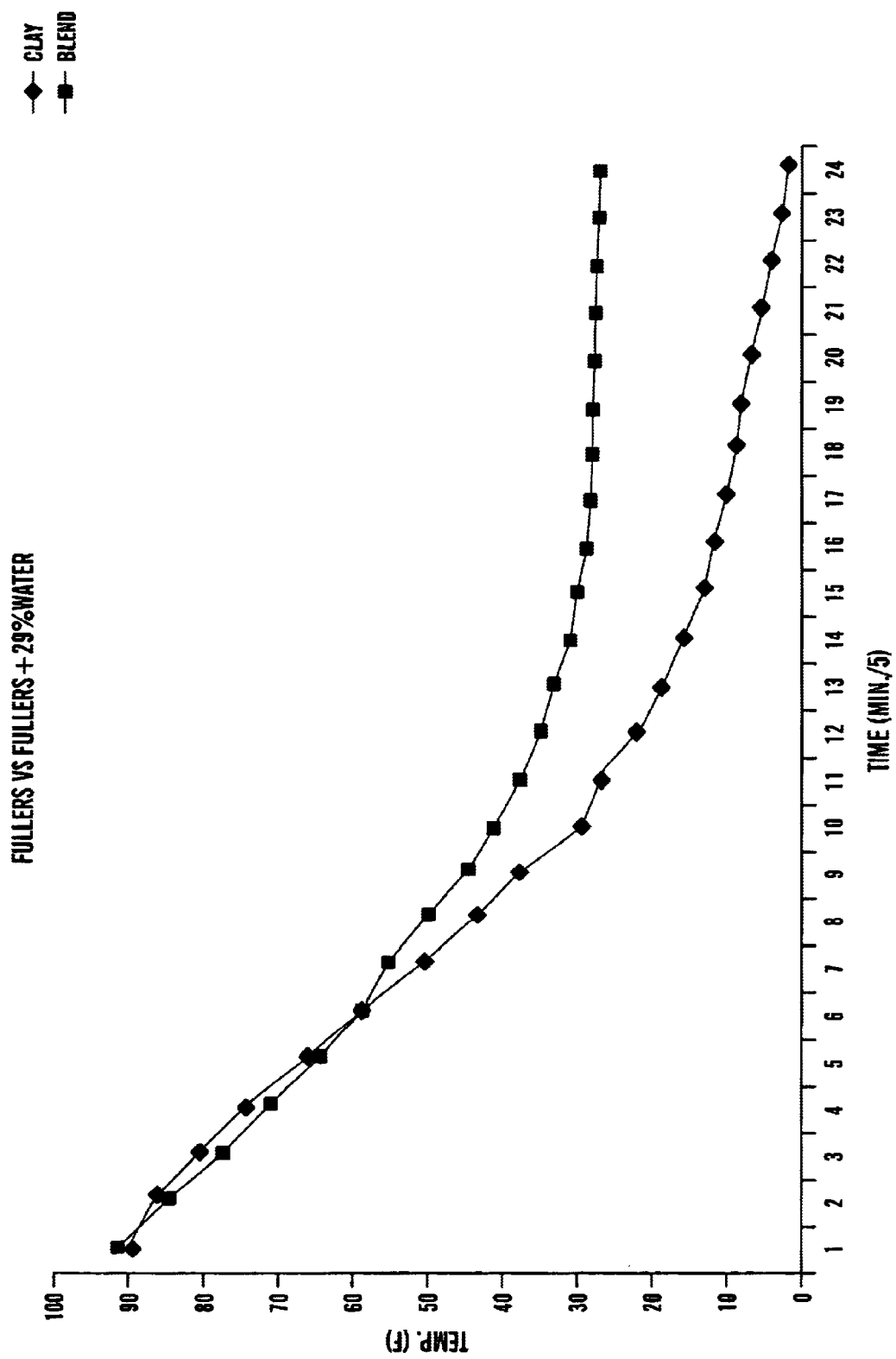
FIG. 1 is a graph showing the time-temperature curve of Fuller's earth and a blend of Fuller's earth and water. This graph depicts an ambient temperature of 0° F. and subsequent freezing of the water bound to Fuller's earth.

The present invention relates to a powdered mix of a phase change material blend. The blend includes a polar phase change material bound substantially to at least one surface of a clay matrix having a surface charge, wherein the blend is present in a powdered form at temperatures above and below the phase change temperature of the polar phase change material.

As used herein, clay matrices are hydrous aluminum silicates, which may contain impurities, such as potassium, sodium, calcium, magnesium, or iron.

In accordance with the present invention, a powdered mix of a phase change material blend comprises a clay matrix as a substrate for a polar phase change material (PCM) that remains loosely bound or powder-like (e.g., like a sand pack), at temperatures above and below the phase change temperature of the PCM. In particular, the clay matrix-PCM blend (i.e., in a powdered form) will not liquefy upon heating of the PCM above its melting point and will not form a rigid solid at temperatures below the melting point of the PCM.

Suitable clay matrices include natural and synthetic clay minerals. In one embodiment, the clay matrix is a phyllosilicate clay. As used herein, phyllosilicates are a group of silicate minerals in which the $SiO_4$ tetrahedra are linked together in flat, infinite sheets (i.e., layer silicates). As described below, the phyllosilicates provide a large surface area per weight of material. In addition, the flat surfaces of the sheets of the phyllosilicates include cations (i.e., interlayer cations) that can produce surface polarity on these sheets. Polar materials, such as polar phase change materials, are attracted to the surface charge of the clay sheets. The number of layers of phase change material that bind to the interlayer surfaces of these clays depends on the nature of the interlayer cations. For example, calcium predominant phyllosilicates hold more water than sodium predominant phyllosilicates.

Useful synthetic types of clay include a synthetic hectorite, which is a layered hydrous magnesium silicate, such as Laponite® (Southern Clay Products, Gonzales, Tex.), a synthetic mica-montmorillonite, such as Barasym® (Baroid Division, NL Industries, Houston, Tex.), and mixtures thereof. Useful natural types of clay include swelling clays such as aliettite, beidellite, nontronite, saponite, sauconite, stevensite, swinefordite, volkonskoite, yakhontovite, hectorite, montmorillonite (such as BP colloid), bentonite, Fuller's earth, and mixtures thereof.

Suitable phyllosilicates include smectite clays, chlorite clays, bentonite, Fuller's earth, attapulgite, mica clays, and combinations thereof. Members of the smectite clay mineral group are distinguished by a large surface area ("S") and the ability to exchange cations, specified by the cation exchange capacity ("CEC") (which has units of milliequivalents (meq)/100 grams of clay). The high surface areas of these materials results from three factors: 1) the small particle size which creates a large external surface area, 2) the ability of the clay layers to expand by incorporating between adjacent layers water and various organic liquids which create a large internal surface area and 3) the plate-like morphology of the smectite clay minerals. Smectite clay minerals are layer structures, of the 2:1 type, which have a net negative charge as the result of substitutions of different cations within the individual mineral sheets. The negative charge on the individual layers is balanced by cations, such as sodium, calcium, and magnesium, which are adsorbed onto both the external and internal surfaces of the clay layers. The CEC of smectite clays typically varies between approximately 50 and 150 meq/100 grams. Suitable smectite clays include, but are not limited to, hectorite, montmorillonite, saponite, and combinations thereof. The smectite clays exhibit a surface charge of from about 0.25 to about 0.6 and a crystal size of from about 0.2 microns to about 2 microns. The larger crystal size is a benefit in processing and handling of the matrix. In particular, the incidence of airborne particulates is minimized and the risk of inhaling the particles is less, as compared to microsilicate particles. In addition, bentonites and Fuller's earth, which are combinations of clay minerals and have smectite clays as a component, are also suitable. Suitable mica clays include vermiculite. The mica clays exhibit a surface charge of from about 0.6 to about 0.9.

Examples of specific types of clays from the smectite mineral group include: hectorite ("SHCa-1", the Source Clay Minerals identification code) (available from the Source Clay Minerals Repository, University of Missouri, Columbia, Mo.) with a CEC=43.9 meq/100 g and S=63.2 $m^2/g$; Cheto montmorillonite ("SAz-1") with a CEC=120 meq/100 g and S=97.4 $m^2/g$; Washington montmorillonite ("SWa-1"); Wyoming montmorillonite ("SWy-2") with a CEC=76.4 meq/100 g, S=31.8 $m^2/g$; Laponite® RD with a CEC=73 meq/100 g and S=330 $m^2/g$; and Laponite® RDS with a CEC=73 meq/100 g and S=360 $m^2/g$.

The clay matrices of the present invention typically have a particle size of about 2 to about 20 microns.

Suitable polar phase change materials (PCMs) include, but are not limited to, water, alcohols (e.g., glycerol), hydrocarbons (e.g., paraffin), hydrated salts, the clathrates, semi-clathrates, gas clathrates, ethylene glycol, polyethylene glycol, and combinations thereof (see, e.g., U.S. Pat. No. 5,106,520 to Salyer, which is hereby incorporated by reference in its entirety). Any polar substance, inorganic or organic, that changes from solid to liquid can be used as the phase change material. The temperature at which the PCM solidifies and the amount of heat released (or absorbed with melting), determines the clay matrix-PCM properties. Alternatively, the phase change temperature of the blend of the present invention may be modified by combining two or more PCMs with different phase change temperatures.

The phase change temperature of the PCM varies with the particular use to which the end product containing the blend of the present invention is to be put. Phase change temperatures of from about 10° C. to about 30° C. may have value in building products. In one embodiment, the PCM has a phase change temperature which is approximately equal to the average human comfort temperature, e.g., 20° C. to 22° C.

In one embodiment, the clay matrix is present in an amount of from about 60 wt. % to about 95 wt. % and the polar phase change material is present in an amount of from about 5 wt. % to about 40 wt. %.

In accordance with the present invention, the PCM binds substantially to at least one surface of the clay matrix. In particular, for a phyllosilicate clay matrix, a polar PCM binds to exchangeable cations on the interlayer surfaces of the clay. For example, water binds to the exchangeable cations of vermiculite as two types (see, e.g., Theng, *The Chemistry of Clay-Organic Reactions,* John Wiley & Sons, New York, pp. 13–15 and 18–20 (1974), which is hereby incorporated by reference in its entirety). The first type is directly coordinated to the cation. The second type forms an outer coordination sphere and is indirectly linked to the cation. Although not wishing to be bound by theory, it is likely that the second type of bound water accounts for the majority of the phase change water.

The phase change material blend of the present invention is a conformable, loosely bound or powder-like composite. In particular, the clay matrix-PCM composite will not liquefy upon heating of the PCM above its melting point and will not form a rigid solid at temperatures below the melting point of the PCM. The blend may be used in building materials, textiles, sports, medicine, agriculture, and other areas where heat energy needs to be released or absorbed at a near constant temperature. In particular, the phase change material blend may be used as part of a therapy pack, as described in detail below, as an additive for soil, in combination with building materials, or as a filler in products for heat regulation. For example, the phase change material blend may be added to soil surrounding plants to provide protection from cold temperatures. In another embodiment, the phase change material blend may be placed adjacent to building materials, such as walls, roofs, or floors, to provide heat retention. Alternatively, the phase change material blend may be used as a filler in any product, e.g., food containers, for which cooling or heating capabilities may be desired. For example, the phase change material blend may be used as a filler in food containers for shipping or serving the food. The blend can be poured, formed, or placed in firm or flexible containers to produce desired products. The phase change material blend of the present invention demonstrates a latent heat energy transfer at about the PCM phase change temperature.

The present invention also relates to a method of making a powdered mix of a phase change material blend. The method includes mixing a clay matrix having a surface charge with a polar phase change material under conditions effective to bind the polar phase change material substantially to at least one surface of the clay matrix in a powdered form at temperatures above and below the phase change temperature of the polar phase change material.

In this embodiment of the present invention, the PCM is mixed with the clay matrix above the melting point of the PCM.

Another embodiment of the present invention relates to a therapy pack including an outer material encapsulating a powdered mix of a phase change material blend, wherein the phase change material blend includes a polar phase change material bound substantially to at least one surface of a clay matrix having a surface charge and wherein the blend is present in a powdered form at temperatures above and below the phase change temperature of the polar phase change material.

Suitable outer materials for this embodiment of the present invention include flexible and/or fluid impervious materials. Such outer materials include, but are not limited to, polyethylene, polyesters, butadieneacrylonitrile copolymers, vinyl polymers, and ethylene-vinyl acetate copolymers.

The use of a flexible outer material allows the therapy pack, when placed against an object, to conform to the contours of the object. In particular, when used as a hot or cold medical wrap or as a plant wrap, the use of a flexible outer material allows the therapy pack to conform to the contours of the body or plant part against which it is placed.

The therapy pack of the present invention may be in the form of a medical pack, a plant pack, or a textile product. In particular, the therapy pack may be in the form of a medical pack useful in the medical treatment of wounds or injuries. In one embodiment, the medical pack may be a joint wrap, e.g., an elbow or knee wrap, for a human body. In another embodiment, the medical pack may be shaped to fit a particular body part, such as the eyes or breast. In this embodiment, the medical pack would be shaped, for example, as small round packs for the eyes or conical or annular packs for the breasts. A medical pack in accordance with the present invention may be used for cold therapy, e.g., for postoperative care, post-injury care, pre- or post-physical therapy care, pre- or postmassage therapy care, or for sports medicine care (i.e., like an ice pack). In addition, a medical pack in accordance with the present invention may be used for heat therapy, i.e., a warming blanket, as described below.

Alternatively, the therapy pack may be in the form of a plant pack, e.g., for a tree or shrub, that is placed around the base of the plant to prevent heat or cold damage. The plant pack is applicable for the growing or shipping of plants.

In yet another embodiment, the therapy pack may be in the form of a textile product, such as a wearable garment (e.g., a coat or other clothing) or a blanket (e.g., a warming blanket). In this embodiment, the textile product may include at least one pouch, either sewn into the product or attached thereto by other means, including the therapy pack of the present invention. Alternatively, a plurality of small channels including the therapy pack of the present invention may be sewn into a fabric. The textile product then releases heat to the user or absorbs heat from the user at a desired temperature. A warming blanket in accordance with the present invention may be used, for example, for anesthetized, traumatized, or newborn patients or as an outdoor recreation warming blanket.

The medical pack, plant pack, or textile garment in accordance with the present invention may include suitable fastener mechanisms, such as adhesive tape, liquid adhesive materials, and hook and loop type fasteners (e.g., Velcro™), for placing the medical pack, plant pack, or textile garment around the desired anatomical body part or plant part.

In accordance with the present invention, the therapy pack may include an insulation layer adjacent and in contact with at least a portion of an outer surface of the outer material. The insulation layer is used to minimize undesirable heat loss or gain from the environment. Suitable insulation materials for the insulation layer include, but are not limited to, polyurethane foam and polystyrene foam.

EXAMPLES

Example 1

Fuller's Earth (Matrix)—Water (PCM) System

Figure 2:
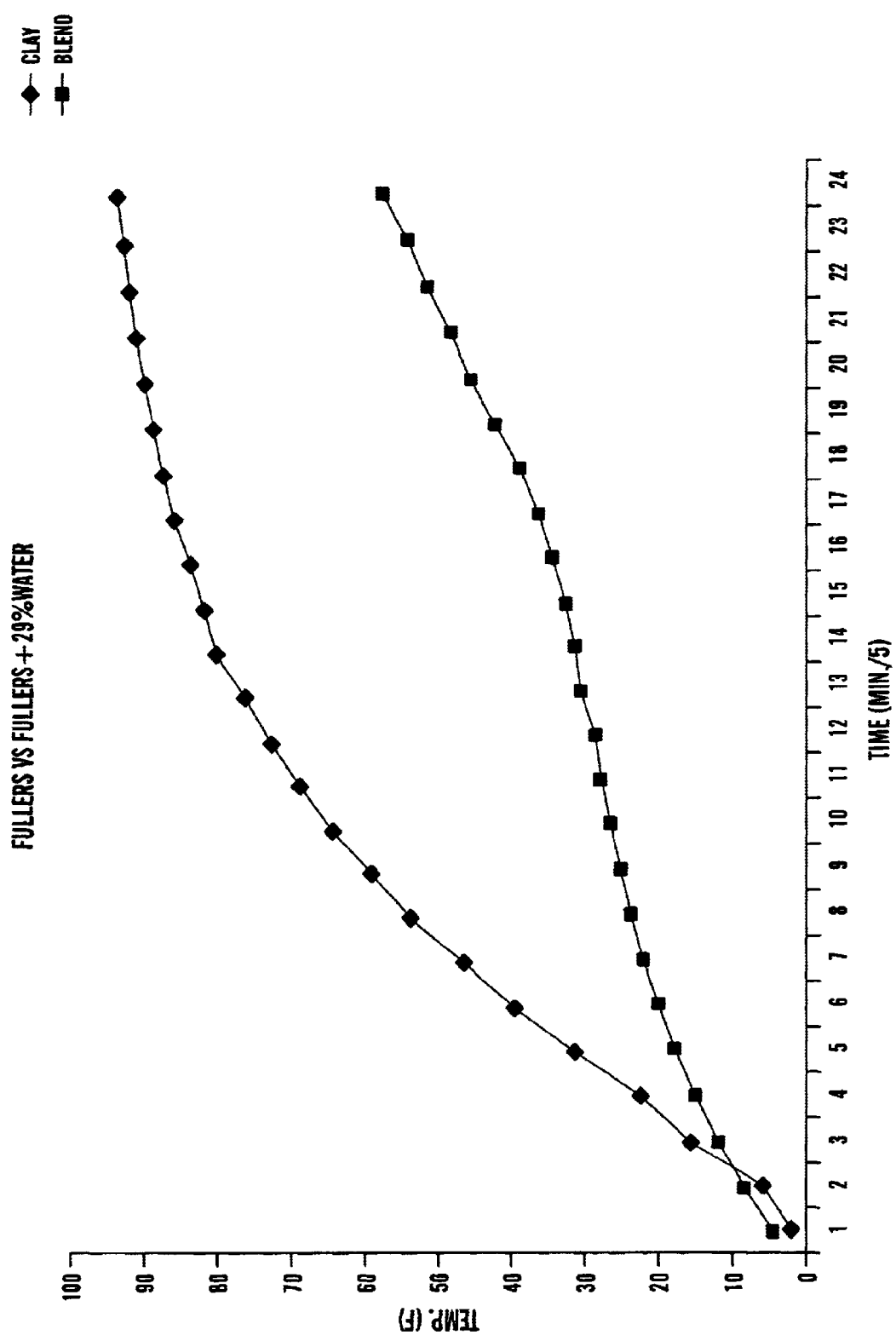
FIG. 2 is a graph showing the time-temperature curve of Fuller's earth and a blend of Fuller's earth and water. This graph depicts an ambient temperature of 94° F. and subsequent thawing of the water bound to Fuller's earth.

A phase change material (PCM) blend including Fuller's earth and water was produced. The blend included 177.5 g Fuller's earth clay (matrix) and 72.5 g water (PCM). Time-temperature curves comparing the matrix alone (i.e., 250 g Fuller's earth clay) and the blend were then produced (see FIGS. 1 and 2). As shown in FIGS. 1 and 2, for the matrix without the PCM, the temperature of the material tended toward the ambient temperature (0° F. in FIG. 1 and 94° F. in FIG. 2) in a simple manner proportional to the sensible heat capacity of the material. However, for the matrix with the PCM, the temperature of the material tended toward the ambient temperature (0° F. in FIG. 1 and 94° F. in FIG. 2) in a simple proportional manner until near the PCM phase change temperature. At this point, the time-temperature curve flattened while heat was transferred as a result of the PCM heat of fusion (or melting). Thus, the total amount of heat absorbed (or lost) was substantially greater for the material with the PCM. After the PCM had changed phase, then the time-temperature curve again resumed a simple proportional curve (see FIG. 2). The PCM blend remained as a dry powdered mix throughout the temperature range.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A powdered mix of a phase change material blend comprising:
    a polar phase change material bound substantially to at least one surface of a clay matrix having a surface charge to form a blend, wherein the blend is present in a powdered form at temperatures above and below a phase change temperature of the polar phase change material.

2. The powdered mix of a phase change material blend according to claim 1, wherein the clay matrix is a phyllosilicate.

3. The powdered mix of a phase change material blend according to claim 2, wherein the phyllosilicate is selected from the group consisting of smectite clays, chlorite clays, bentonite, Fuller's earth, attapulgite, mica clays, and combinations thereof.

4. The powdered mix of a phase change material blend according to claim 2, wherein the polar phase change material is bound to at least one interlayer surface of the phyllosilicate.

5. The powdered mix of a phase change material blend according to claim 1, wherein the polar phase change material is selected from the group consisting of water, alcohols, hydrocarbons, hydrated salts, clathrates, semiclathrates, gas clathrates, ethylene glycol, polyethylene glycol, and combinations thereof.

6. The powdered mix of a phase change material blend according to claim 1, wherein the clay matrix is present in an amount of from about 60 wt. % to about 95 wt. % and wherein the polar phase change material is present in an amount of from about 5 wt. % to about 40 wt. %.

7. A method of making a powdered mix of a phase change material blend comprising:
    mixing a clay matrix having a surface charge with a polar phase change material under conditions effective to bind the polar phase change material substantially to at least one surface of the clay matrix in a powdered form at temperatures above and below a phase change temperature of the polar phase change material.

8. The method according to claim 7, wherein the clay matrix is a phyllosilicate.

9. The method according to claim 8, wherein the phyllosilicate is selected from the group consisting of smectite clays, chlorite clays, bentonite, Fuller's earth, attapulgite, mica clays, and combinations thereof.

10. The method according to claim 8, wherein the polar phase change material is bound to at least one interlayer surface of the phyllosilicate.

11. The method according to claim 7, wherein the polar phase change material is selected from the group consisting of water, alcohols, hydrocarbons, hydrated salts, clathrates, semi-clathrates, gas clathrates, ethylene glycol, polyethylene glycol, and combinations thereof.

12. The method according to claim 7, wherein said mixing comprises mixing from about 60 wt. % to about 95 wt. % clay matrix with from about 5 wt. % to about 40 wt. % polar phase change material.

13. A therapy pack comprising:
    an outer material encapsulating a powdered mix of a phase change material blend, wherein the phase change material blend comprises a polar phase change material bound substantially to at least one surface of a clay matrix having a surface charge and wherein the blend is present in a powdered form at temperatures above and below a phase change temperature of the polar phase change material.

14. The therapy pack according to claim 13, wherein the clay matrix is a phyllosilicate.

15. The therapy pack according to claim 14, wherein the phyllosilicate is selected from the group consisting of smectite clays, chlorite clays, bentonite, Fuller's earth, attapulgite, mica clays, and combinations thereof.

16. The therapy pack according to claim 14, wherein the polar phase change material is bound to at least one interlayer surface of the phyllosilicate.

17. The therapy pack according to claim 13, wherein the polar phase change material is selected from the group consisting of water, alcohols, hydrocarbons, hydrated salts, clathrates, semi-clathrates, gas clathrates, ethylene glycol, polyethylene glycol, and combinations thereof.

18. The therapy pack according to claim 13, wherein the clay matrix is present in an amount of from about 60 wt. % to about 95 wt. % and wherein the polar phase change material is present in an amount of from about 5 wt. % to about 40 wt. %.

19. The therapy pack according to claim 13, wherein the outer material is flexible.

20. The therapy pack according to claim 13, wherein the outer material is selected from the group consisting of polyethylene, polyesters, butadieneacrylonitrile copolymers, vinyl polymers, and ethylene-vinyl acetate copolymers.

21. The therapy pack according to claim 13 further comprising:
    an insulation layer adjacent and in contact with at least a portion of an outer surface of the outer material.

* * * * *